United States Patent [19]

Vescovini

[11] Patent Number: 5,147,544
[45] Date of Patent: Sep. 15, 1992

[54] BLOOD FILTER IN MEDICAL DEVICES
[75] Inventor: Pietro Vescovini, Medolla, Italy
[73] Assignee: Dideco S.r.l., Italy
[21] Appl. No.: 691,938
[22] Filed: Apr. 26, 1991
[30] Foreign Application Priority Data May 2, 1990 [IT] Italy ................................ 20181 A/90

[51] Int. Cl.⁵ .............................................. B01D 35/00
[52] U.S. Cl. .................................... 210/438; 210/311; 210/437; 210/456; 210/457; 210/493.1; 422/101
[58] Field of Search ................ 210/188, 437, 438, 446, 210/456, 493.1, 493.5, 308, 309, 457, 458, 311, 439; 422/101

[56] References Cited

U.S. PATENT DOCUMENTS

| | | | |
|---|---|---|---|
| 1,194,646 | 8/1916 | Linden | 210/311 |
| 3,912,533 | 10/1975 | Heyer | 210/311 |
| 4,560,477 | 12/1985 | Moldow | 210/493.1 |
| 4,663,125 | 5/1987 | Gordon et al. | 210/493.5 |
| 4,664,682 | 5/1987 | Monzen | 210/188 |
| 4,758,337 | 7/1988 | Köhn et al. | 210/493.1 |
| 4,919,802 | 4/1990 | Katsura | 210/456 |
| 4,954,255 | 9/1990 | Müller et al. | 210/493.5 |
| 4,964,984 | 10/1990 | Reeder et al. | 210/456 |

Primary Examiner—Robert A. Dawson
Assistant Examiner—Sun Uk Kim
Attorney, Agent, or Firm—Kenyon & Kenyon

[57] ABSTRACT

The invention relates to a generally cylindrically shaped container having a filter medium positioned therein and a plurality of partitions, each extending upwardly from the bottom of the container providing a plurality of adjacent lower sections to include an inlet section within the container. The inlet section has an inlet port on one side of the filter medium interconnecting the inlet section with the inlet of the container, and each of the sections has an outlet port on the other side of the filter medium. When blood is introduced into the filter, the blood flows initially and at low flow rates only through the inlet section, and at sufficiently higher flow rates the blood level exceeds the height of the partition of the inlet section and further flows successively over the partitions and through the adjacent sections.

5 Claims, 2 Drawing Sheets

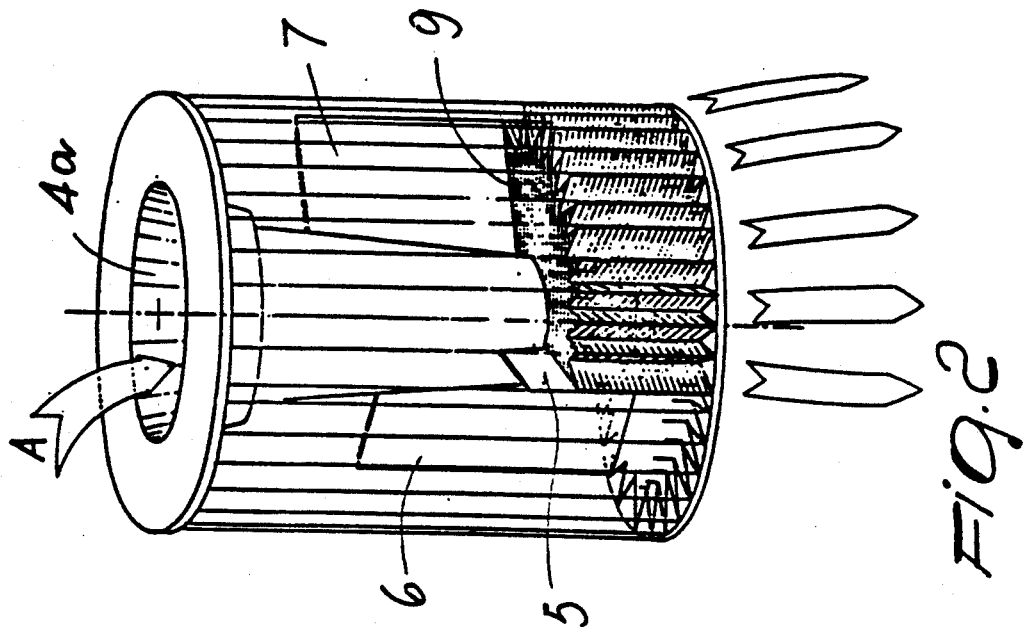
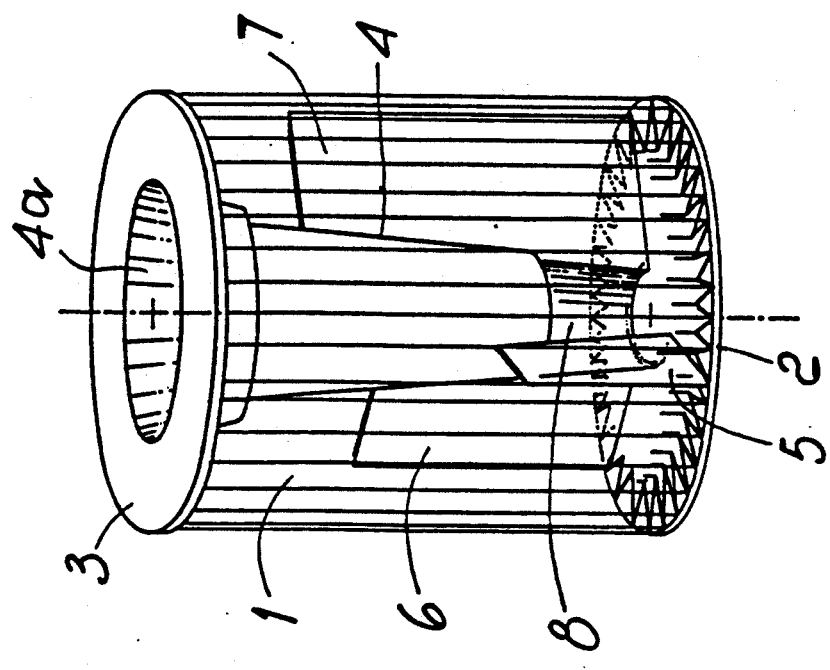

BLOOD FILTER IN MEDICAL DEVICES

BACKGROUND OF THE INVENTION

The invention relates to a blood filter in medical devices.

It is known that in a very large number of medical devices there is a filter wherethrough blood passes during extracorporeal circulation from a patient.

Such filters have varied structural forms and dimensions so that they can operate throughout an entire range of blood flow from the minimum to the maximum flow rates. However, the filters of the prior art have several disadvantages.

One of these disadvantages is that when blood passes through the filter at the near-minimum flow-rate for which the filter has been dimensioned, the filter is filled by blood over a large percentage of its filtration medium surface, which is physiologically unfavorable.

A second disadvantage in near-minimum flow-rate conditions is the amount of time required for adequate hydraulic head pressure for the flow of blood through the filter.

Another disadvantage of known filters is the large internal volume which requires a high value of priming, i.e. of the amount of blood contained in the extracorporeal circuit.

An object of the present invention is therefore to provide a blood filter wherein the amount of filtration medium surface involved is optimally adjusted according to the flow-rate of the blood which passes through the filter, and wherein the optimum head is quickly obtained, even for low blood flow-rates.

SUMMARY OF THE INVENTION

The proposed objective is achieved by a blood filter in medical devices, according to the present invention, which comprises a generally cylindrically shaped container having a top, a bottom and an inlet; a filter medium positioned within said container between the top and bottom thereof; a plurality of partitions, each extending upwardly from the bottom of said container and not extending to the top thereof, providing a plurality of adjacent lower sections to include an inlet section within said container, wherein the inlet section has an inlet port on one side of said filter medium interconnecting said inlet section with said inlet, and each of the sections has an outlet port on the other side of the said filter medium; whereby when blood is introduced into said filter, the blood flows initially and at low flow rates only through the inlet section, and at sufficiently higher flow rates the blood level exceeds the height of the partition of the inlet section and further flows successively over the partitions and through the adjacent sections.

DETAILED DESCRIPTION OF THE INVENTION

Further characteristics and advantages will become apparent from the description of a preferred but not exclusive embodiment of the invention, illustrated only by way of non-limitative example in the accompanying drawings, wherein:

FIG. 1 is a top front perspective view of an empty transparent filter, with the elements comprised within the filter indicated in phantom lines;

FIG. 2 is a top perspective view of the filter in the operating condition which occurs in the presence of a small flow-rate of blood;

Figure 4:
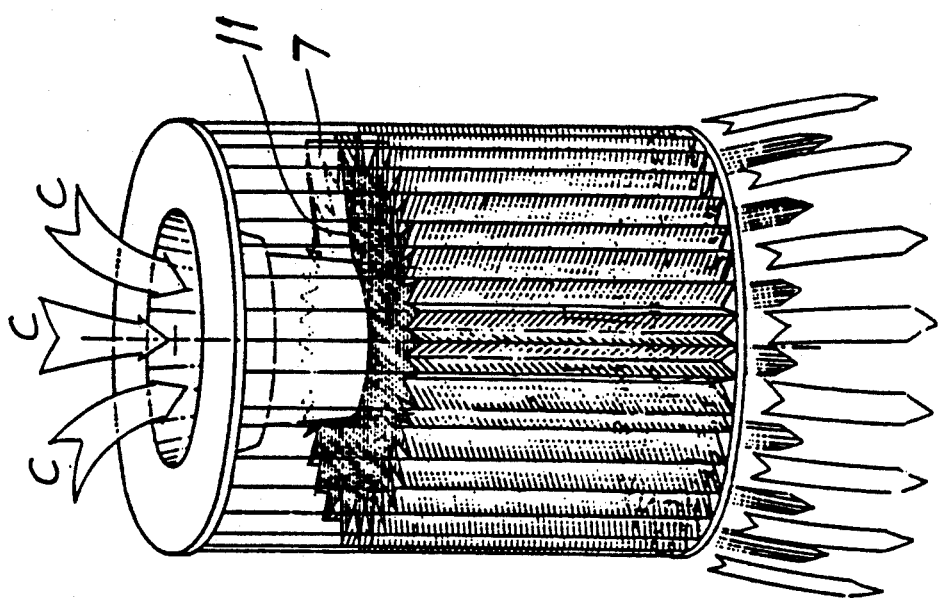
FIG. 4 is a top perspective view of the filter in the operating condition which occurs with a large flow-rate of blood.

With reference to the above figures, a filter medium 1, formed by a sheet of a suitable pleated material, is arranged in a cylindrically shaped container and retained by the bottom 2 and by the top 3 of the container. The container includes an interior chamber 4 having an upper inlet 4a for the inflow of the blood into the filter.

The portion of space surrounded by the filter medium 1 is divided into three sections by three fin type partitions 5, 6, 7 which extend from the bottom 2 and, in that order, have a progressive increase in height but in any case do not touch the top 3.

In the section defined by the partitions 5 and 7, the inlet section, there is, in the chamber 4, an inlet port 8 for inter-connecting this section with the chamber 4 for the inflow of the blood into the filter.

Figure 3:
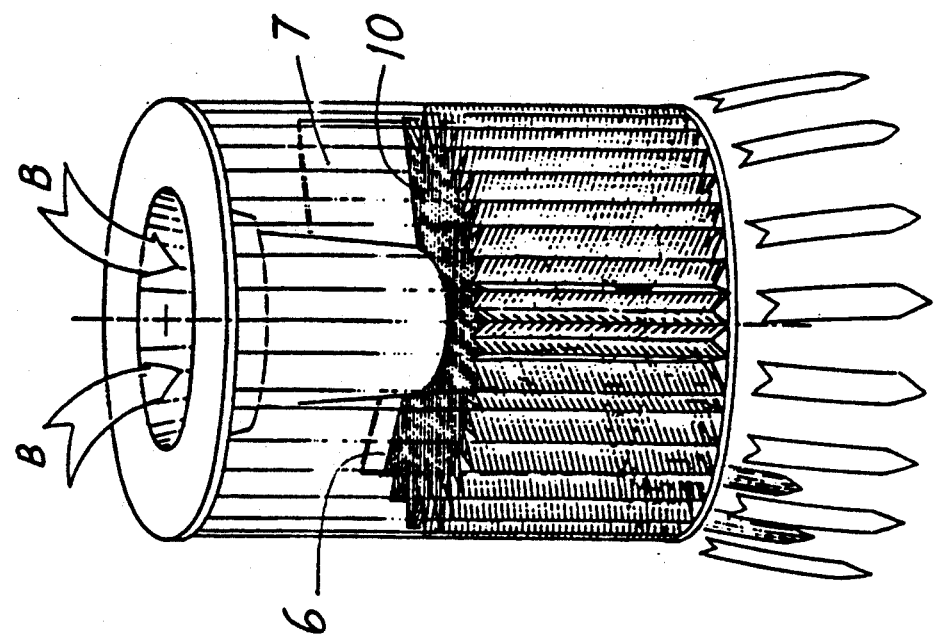
FIG. 3 is a top perspective view of the filter in the operating condition which occurs with a medium flow-rate of blood.

The operation of the invention is shown in FIGS. 2, 3 and 4. FIG. 2 illustrates an operating condition characterized by a low flow-rate of blood, visually represented by the presence of a single arrow A directed toward the inside of the inflow chamber 4. It can be seen that the only portion of filter involved in the operation is the inlet section. This occurs because the level 9 corresponding to a hydraulic head of the blood which ensures the correct operation of the filter in this flow-rate condition is not such as to exceed the height of the partition 5.

FIG. 3 illustrates the condition of a medium blood flow-rate, indicated by the presence of the two arrows B; in this situation, two sections of the filter medium are involved, because the level 10 of the blood which ensures the optimum operating conditions exceeds the height of the partition 5 but not that of the partition 6. The blood thus flows in through the inlet port 8 filling the inlet section between the partitions 5 and 7 and spilling over the top of the partition 5 and into the adjacent section defined by the partitions 5 and 6 wherein it reaches the level 10 indicating the desired optimum operating condition.

FIG. 4 finally illustrates the condition which occurs in the case of a large flow-rate, indicated by the three arrows C; in this case the level 11 of blood which is achieved in the filter is such as to also exceed the height of the partition 6, and so all three sections of the filter are involved in the blood filtering operation.

From what has been described it is evident that the blood which passes through the filter makes contact, for every flow-rate value which can occur, with a filtration surface which is optimally self-adjusted to the flow-rate. It is also evident that the head required for the correct passage is quickly achieved in the inlet section.

It can thus be seem that in the case of the low flow-rate the blood occupies only one of the three sections of the filter, and thus makes contact with a small filtration surface and which forms a good hydraulic head in a very short time. The filtration surface involved in the operation increases only when the flow-rate of blood increases.

A favorable operating condition can also occur in the described filter if the first section involved in the passage of blood should lose filtration capacity due to clogging; in this case the blood level inside the filter would naturally increase and blood would occupy the second section as well, automatically restoring a good filtration efficiency.

Finally, the reduction in priming, which the filter according to the invention allows one to obtain at low and medium flow-rates, should be stressed.

The described invention is susceptible to numerous modifications and variations, all of which are within the scope of the inventive concept. Thus, for example, the number of partitions may be varied, and furthermore said partitions might have a constant height; the connecting port between the blood inflow chamber and one of the partitions of the filter medium might furthermore be arranged in an elevated position instead of adjacent to the bottom.

In the practical embodiment of the invention, all the details may be replaced with other technically equivalent elements; the materials employed, as well as the shapes and dimensions, may furthermore be any.

I claim:

1. A blood filter comprising:
   a generally cylindrically shaped container having a top, a bottom, and an inlet;
   a filter medium positioned within said container between the top and bottom thereof;
   a plurality of partitions, each extending upwardly from the bottom of said container toward the top thereof, providing a plurality of adjacent lower sections to include an inlet section within said container,
   wherein the inlet section has an inlet port on one side of said filter medium interconnecting said inlet section with said inlet, and each of the sections has an outlet port on the other side of the said filter medium;
   whereby when blood is introduced into said filter, the blood flows initially and at low flow rates only through the inlet section, the inlet section opening into one lower section so the other sections are fed only by spilling over the top of one or more partitions with blood flow at sufficiently higher flow rates the blood level exceeds the height of one or more partitions of the inlet section and further flows successively thereover and through the adjacent sections.

2. The filter of claim 1 wherein said partitions extend to a generally constant height.

3. The filter of claim 1 wherein said partitions extend at relatively different heights.

4. The filter of claim 1 wherein said partitions extend at gradually increased heights, wherein said inlet section is defined between said partitions having respectively minimum and maximum heights.

5. The filter of claim 1 which has three said partitions.

* * * * *